United States Patent [19]

Finger

[11] Patent Number: Plant 6,648

[45] Date of Patent: Mar. 7, 1989

[54] KALANCHOE PLANT NAMED CHARME

[75] Inventor: Hermann Finger, Wiesmoor, Fed. Rep. of Germany

[73] Assignee: Wiesmoor-Gartnerie und Baumschule GmbH, Wiesmoor, Fed. Rep. of Germany

[21] Appl. No.: 108,983

[22] Filed: Oct. 16, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Kalanchoe plant named Charme, having relatively small, bright deep pink flower color, compact growth habit with superior basal branching, relatively small but dense dark green leaves, large flower head and floriferous habit, and by its ability to flower over a long period of time in the home environment.

1 Drawing Sheet

The present invention relates to a new and distinctive cultivar of Kalanchoe plant, botanically known as *Kalanchoe blossfeldiana*, and known by the cultivar name Charme. Charme was developed by me through controlled breeding in Wiesmoor, Federal Republic of Germany by crossing Singapur (U.S. Plant Pat. No. 5,361), the seed parent, with Bali (U.S. Plant Pat. No. 5,348), the pollen parent.

Asexual reproduction by me in Wiesmoor, Federal Republic of Germany by stem cuttings of Charme of a selection from the progeny of the stated cross has shown that the unique features of this new Kalanchoe are stabilized and are reproduced true to type in successive propagations.

The following characteristics distinguish Charme from both its parent varieties and other cultivated Kalanchoes of this type known and used in the floriculture industry:

1. Charme is characterized by its distinct bright deep pink flower color. Bingo (U.S. Plant Pat. No. 5,876) has lighter pink flowers while Sensation (U.S. Plant Pat. No. 4,727), Cherry Jubilee (U.S. Plant Pat. No. 5,877) and Satisfaction (U.S. Plant Pat. No. 5,894) have rose-purple flowers, and Singapur (U.S. Plant Pat. No. 5,361) has rose red flowers.

2. Flower size of Charme is smaller than the rest of the comparison cultivars but there are more flowers in the flower head. Thus, Charme produces a very good show of color.

3. Charme has more pointed, narrow flower petals, similar to Satisfaction, while Sensation, Bingo, Cherry Jubilee, and Singapur have more rounded petals.

4. Charme is more compact and has superior basal branching compared to the five comparison cultivars.

5. Charme is similar in maturity to Sensation and Satisfaction, while Bingo, Cherry Jubilee, and Singapur are approximately one week earlier.

6. Charme has the smallest leaves and the most dense plant growth of any of these cultivars, with Bingo having slightly larger leaves and Cherry Jubilee, Sensation, Satisfaction, and Singapur having much larger leaves.

7. Charme has dark green leaves, as does Bingo, with Cherry Jubilee, Sensation, Satisfaction, and Singapur having a lighter yellow green leaf.

8. Charme has a very large, heavily branched flower head, with Bingo, Singapur, and Cherry Jubilee having a somewhat more open, less branched cluster and Sensation and Satisfaction having an even more open and less full head.

9. To applicant's knowledge, Charme is the only cultivar that exhibits branching on the lateral branches.

10. Charme has exhibited the ability to continue flowering for a long period of time under less than ideal conditions of the home environment.

The accompanying colored photograph illustrates in top perspective view the overall appearance of Charme, with colors being as true as it is reasonably possible to obtain in a colored reproduction of this type.

The following is a detailed description of my new Kalanchoe variety based on plants produced under commercial practices in Wiesmoor, Federal Republic of Germany and Ashtabula, Ohio. Color references are made to The Royal Horticultural Society Colour Chart, except where general colors of ordinary dictionary significance are used.

Parentage: A controlled cross between the female parent Singapur and the male parent Bali.

Propagation:

(A) *Type cutting.*—2 cm long stem tip cutting.

(B) *Time to root.*—10 days at 21° C. summer. 14 days at 21° C. winter.

(C) *Rooting habit.*—Abundant; fine, fibrous roots.

Plant description:

(A) *Form.*—Short, compact, almost no elongation of main stem; excellent basal branching, with even the basal branches developing flowers; dense foliage growth. Scheduling practices can produce a plant in either a 10 cm or 12 cm pot.

(B) *Habit of growth.*—Shoots form at every node, and because of lack of elongation of main stem the plant has a rosette appearance; very symmetrical plant with flowers above foliage.

(C) *Foliage.*—Leaves simple, opposite. (1) Size: One full grown leaf of a 10 cm flowering plant is 90 mm long and 50 mm wide. (2) Shape: Ovate, apex obtuse, base acute. (3) Texture: Glabrous, succulent, coriaceous. (4) Margin: Crenate. (5) Color: Young foliage, top side 146A, under side 146 A. Mature foliage, top side 147A, under side 147B.

Flowering description:

(A) *Flowering habits.*—Inflorescence is a cyme, terminal flower of the main axis opens first, followed by the terminal flowers of the side branches, continuing with subsequent development of branches in the inflorescence.

(B) *Natural flowering season.*—Early January. Flowering time under controlled daylength at 20° C. in summer is 11 weeks; in winter 13 weeks. Flowering time depends on temperature, light intensity and other growing conditions.

(C) *Flower buds.*—Elliptical to oblong, up to 7 mm long, developing to tubular as flower petals mature, sheathed with four green sepals; corolla at maturity is 5 mm long.

(D) *Flowers borne.*—On compound dichasial cymes, primary peduncle 3 mm in diameter, with peduncle length depending on environment and B-9 application. Pedicles are up to 2 mm in diameter.

(E) *Quantity of flowers.*—One of the most floriferous cultivars to date, with mature flowering plant having over 250 flowers due to its highly branched nature.

(F) *Petals.*—(1) Shape: More long than rounded with acuminate tip. (2) Color: Top side, when opening, 46D, fading to 67C; under side has both 66C and 68C red purple in it. (3) Number of petals: 4.

(G) *Reproductive organs.*—(1) Stamens: Eight (8) in number. (a) Anther shape: Flat, elliptical, color yellow. (b) Filament color: Light green. (c) Pollen color: Yellow. (2) Pistils: (a) Stigma shape: Flat, color whitish when mature. (b) Style color: Yellow green. (c) Ovaries: 4 in number, size 4 mm, color light green.

Disease resistance: No disease problems observed to date.

Other important characteristics: Charme shows resistance to heat delay under blackcloth shading for short day treatment under high temperature conditions. The stems of Charme are not as large in diameter as other cultivars but can hold the smaller flowers up. Excellent 10 cm pot cultivar.

I claim:

1. A new and distinct cultivar of Kalanchoe plant named Charme, as illustrated and described.

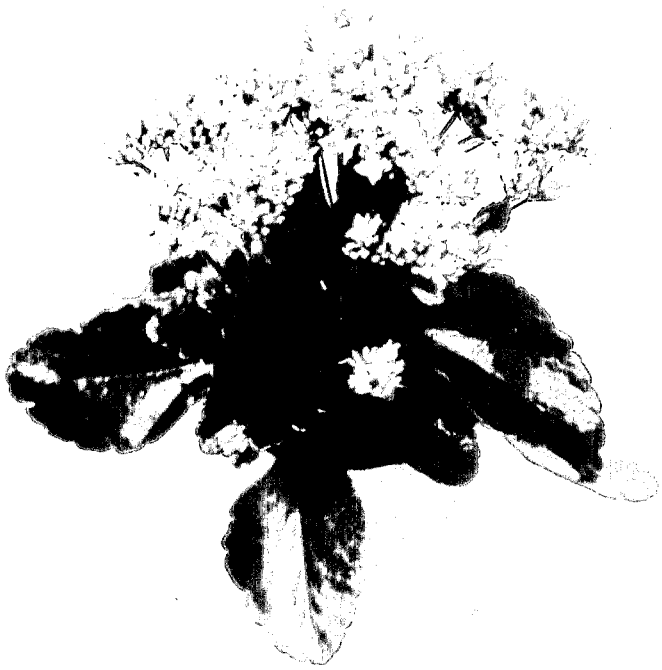

* * * * *